(12) United States Patent
Perez et al.

(10) Patent No.: US 8,236,284 B1
(45) Date of Patent: Aug. 7, 2012

(54) MULTIMODAL, MULTIFUNCTIONAL POLYMER COATED NANOPARTICLES

(75) Inventors: J. Manuel Perez, Orlando, FL (US); Santimukul Santra, Orlando, FL (US)

(73) Assignee: University of Central Florida Research Foundation, Inc., Orlando, FL (US)

( * ) Notice: Subject to any disclaimer, the term of this patent is extended or adjusted under 35 U.S.C. 154(b) by 329 days.

(21) Appl. No.: 12/416,993

(22) Filed: Apr. 2, 2009

Related U.S. Application Data

(60) Provisional application No. 61/161,476, filed on Mar. 19, 2009, provisional application No. 60/041,613, filed on Apr. 2, 2008.

(51) Int. Cl.
*A61K 9/14* (2006.01)
*A01N 59/16* (2006.01)

(52) U.S. Cl. ............... 424/9.323; 424/489; 424/646; 514/502; 977/773; 977/777

(58) Field of Classification Search .................. None
See application file for complete search history.

(56) References Cited

U.S. PATENT DOCUMENTS

| | | |
|---|---|---|
| 2003/0152518 A1* | 8/2003 | Tidmarsh et al. ............. 424/9.6 |
| 2007/0009441 A1* | 1/2007 | Erathodiyil et al. ......... 424/9.34 |
| 2008/0187595 A1 | 8/2008 | Jordan et al. |
| 2008/0268061 A1 | 10/2008 | Jordan et al. |
| 2009/0041674 A1 | 2/2009 | Jones et al. |
| 2009/0068115 A1 | 3/2009 | Gaw et al. |
| 2009/0074671 A1 | 3/2009 | Kojima et al. |

FOREIGN PATENT DOCUMENTS

WO WO 2008125618 A1 * 10/2008

OTHER PUBLICATIONS

S Wan, Y Zheng, Y Liu, H Yan, K Liu. "Fe3O4 Nanoparticles coated with homopolymers of glycerol mono(meth)acrylate and their block copolymers." J Mater Chem, vol. 15, 2005, pp. 3424-3430.*
S Santra, B Liesenfeld, D Dutta, D Chatel, CD Batich, W Tan, BM Moudgil, RA Mericle. "Folate Conjugated Fluorescent Silica Nanoparticles for Labeling Neoplastic Cells." Journal of Nanoscience and Nanotechnology. vol. 5, 2005, 899-904.*
K Riebeseel, E Biedermann, R Loser, N Breiter, R Hanselmann, R Mulhaupt, C Unger, F Kratz. "Polyethylene Glycol Conjugates of Methotrexate Varying in Their Molecular Weight from MW 750 to MW 40000: Synthesis, Characterization, and Structure-Activity Relationships in Vitro and in Vivo." Bioconjugate Chem, 2002, vol. 13, pp. 773-785.*
SD Palma, B Maletto, P Lo Nostro, RH Manzo, MC Pistoresi-Palencia, DA Allemandi. "Potential Use of Ascorbic Acid-Based Surfactants as Skin Penetration Enhancers." Drug Development and Industrial Pharmacy, vol. 32, 2006, pp. 821-827.*

* cited by examiner

*Primary Examiner* — Frederick Krass
*Assistant Examiner* — Isaac Shomer
(74) *Attorney, Agent, or Firm* — Allen, Dyer, Doppelt, Milbrath & Gilchrist, P.A.

(57) ABSTRACT

Disclosed are nanoparticles having a metallic core consisting essentially of superparamagnetic iron oxide; a polymeric coat surrounding said core, the coat having a matrix of polyacrylic acid and forming an outer periphery of said nanoparticle; a plurality of hydrophobic pockets formed by the polymeric coat; a plurality of carboxylic groups along an outer periphery of the polymeric coat and effective to conjugate with a predetermined targeting ligand which functionalizes the nanoparticle; a lipophylic fluorescent dye encapsulated in the plurality of hydrophobic pockets; and a drug encapsulated in the plurality of hydrophobic pockets. Associated methods of making the nanoparticles and of treatments using the nanoparticles are also disclosed.

26 Claims, 15 Drawing Sheets

MULTIMODAL, MULTIFUNCTIONAL POLYMER COATED NANOPARTICLES

RELATED APPLICATION

This application claims priority from co-pending provisional application Ser. No. 61/041,613, which was filed on 2 Apr. 2008, and to provisional application Ser. No. 61/161, 476, which was filed on 19 Mar. 2009 and is incorporated herein by reference in its entirety.

STATEMENT OF GOVERNMENT RIGHTS

Development of the present invention was supported, at least in part, by a grant from the U.S. Government. Accordingly, the Government may have certain rights in the invention, as specified by law.

FIELD OF THE INVENTION

The present invention relates to the field of medical treatment of disease and, more particularly, to multimodal, multifunctional nanoparticles which serve as drug carriers for targeted delivery and which can also be tracked by optical and magnetic resonance imaging.

BACKGROUND OF THE INVENTION

Superparamagnetic iron oxide nanoparticles with dual imaging and therapeutic capabilities hold great promise for the non-invasive detection and treatment of tumors.[1] When conjugated with tumor-specific targeting ligands, these multifunctional nanoparticles can be used to specifically deliver anti-cancer drugs to tumors, thereby minimizing severe side effects.[2] To meet the demand for the rapid development and potential clinical application of targeted anti-cancer nanotherapies, it is desirable to introduce optical (fluorescent) imaging capabilities to these nanoparticles to facilitate non-invasive assessment of drug homing and efficacy. This is often achieved by crosslinking the polymeric coating surrounding the nanoparticle and functionalizing its surface with amine or carboxyl groups that are then used to conjugate fluorescent dyes and drugs.[3] This approach to introduce multimodality (magnetic and fluorescent)[4] and multifunctionality (imaging and therapeutic)[5] to iron oxide nanoparticles (IONPs), although widely used, often compromises the solubility of the nanoparticles in aqueous media and reduces the number of available functional groups that otherwise could be used to attach ligands for targeting applications.

SUMMARY OF THE INVENTION

With the foregoing in mind, the present invention advantageously provides iron oxide nanoparticles (IONPs) wherein a lipophilic near infrared (NIR) dye and an anti-cancer drug are co-encapsulated within hydrophobic pockets formed in a polymeric matrix of polyacrylic acid (PAA) which coats the nanoparticles (PAA-IONPs). The resulting composition is useful for combined optical imaging, MRI detection and targeted cancer therapy.

Our water-based and green chemistry approach to synthesizing these nanoparticles has five components (a) an encapsulated chemotherapeutic agent effective in cancer therapy (for example, paclitaxel, also known by the tradename Taxol), (b) a surface functionality (folic acid ligand) for cancer targeting, (c) "click"-chemistry-based conjugation of targeting ligands, (d) an encapsulated NIR fluorescent dye for imaging capabilities and (e) a superparamagnetic iron oxide core for magnetic resonance imaging (MRI).

Biocompatible, multimodal and theranostically functional IONPs were synthesized using a novel water-based method and demonstrated excellent properties for targeted cancer therapy, optical and magnetic resonance imaging (MRI). For the first time, a facile, modified solvent diffusion method is used for the co-encapsulation of both an anti-cancer drug and near infrared fluorescent dyes. The resulting folate-derivatized theranostic nanoparticles could allow for targeted optical/MR-imaging and targeted killing of folate expressing cancer cells.

Specifically, our synthetic procedure differs from the previously reported methods in that the polymer is not present during the initial nucleation process.[6-8] Instead, the polyacrylic acid is added at a later stage. This "step-wise" process, as opposed to the "in-situ" process, allows for the formation of stable, dispersed and highly crystalline superparamagnetic iron oxide nanocrystals coated with PAA, (step 1, as shown in FIG. 1). Successful coating with PAA was confirmed by the presence of a negative zeta-potential g=−48 mV) and via FT-IR analysis (as shown in FIG. 8). We then hypothesized whether a hydrophobic dye could be encapsulated within the hydrophobic pockets in the PAA coating, to thereby generate multimodal IONPs with dual magnetic and fluorescent properties. As a proof-of-principle, we have encapsulated two lipophilic fluorescent dyes (DiI or DiR) (step 2, as shown in FIG. 1) using a modified solvent diffusion method.[9] These dialkylcarbocyanine fluorophores (DiI, DiR) are widely used in biomedical applications to label cell membranes and were selected because of their high extinction coefficients (c>125, 000 $cm^{-1}$ $M^{-1}$) and high fluorescence in hydrophobic environments.[9] The long chain dialkylcarbocyanine dye, DiR, is of particular importance since it has an excitation/emission near the infrared region (751/780), suitable for in vivo imaging.

Next, the IONPs (1, FIG. 1) were functionalized to yield a propargylated nanoparticles (3, FIG. 1), which were later used to generate multimodal folate-derivatized nanoparticles (4, FIG. 1) via a highly selective 1,3-dipolar cycloaddition reaction ("click" chemistry).[10] Thus, the water-soluble carbodiimide EDC, [1-ethyl-3-(3-dimethylaminopropyl) carbodiimide hydrochloride] was utilized to prepare the propargylated IONP (3, FIG. 1), which is an important synthon for the synthesis of a library of functional IONPs via "click" chemistry. The presence of a weak 'C≡C' band at 2265 $cm^{-1}$ in the FT-IR spectrum of these nanoparticles confirmed the presence of a propargyl (triple bond) group (FIG. 9).

As a model system, we conjugated the nanoparticles 3 with an azide-functionalized folic acid[11] analog (FIG. 6) via "click" chemistry. The resulting folate-decorated IONPs are soluble in aqueous media and can encapsulate lipophilic fluorescent dyes. The presence of folic acid and dye in these multimodal folate-derivatized nanoparticles (4, Scheme 1) was confirmed through various spectrophotometric studies (FIGS. 10-12). Furthermore, a hydrophobic anti-cancer drug (paclitaxel, a.k.a. Taxol®) was encapsulated to yield a theranostic (therapeutic and diagnostic) nanoparticle with dual imaging and therapeutic properties (5, Scheme 1). These functional IONPs (1-5) were highly stable in aqueous solutions, as their magnetic relaxivity (R2), hydrodynamic diameter (D) and polydispersity index (PDI) remained unaffected over a long period of time (Table 3). Therefore, the versatility of the present method allows the generation of a small library of multifunctional, multimodal and targetable IONPs.

BRIEF DESCRIPTION OF THE DRAWINGS

Some of the features, advantages, and benefits of the present invention having been stated, others will become apparent as the description proceeds when taken in conjunction with the accompanying drawings, presented for solely for exemplary purposes and not with intent to limit the invention thereto, and in which.

DETAILED DESCRIPTION OF THE PREFERRED EMBODIMENT

Figure 1:
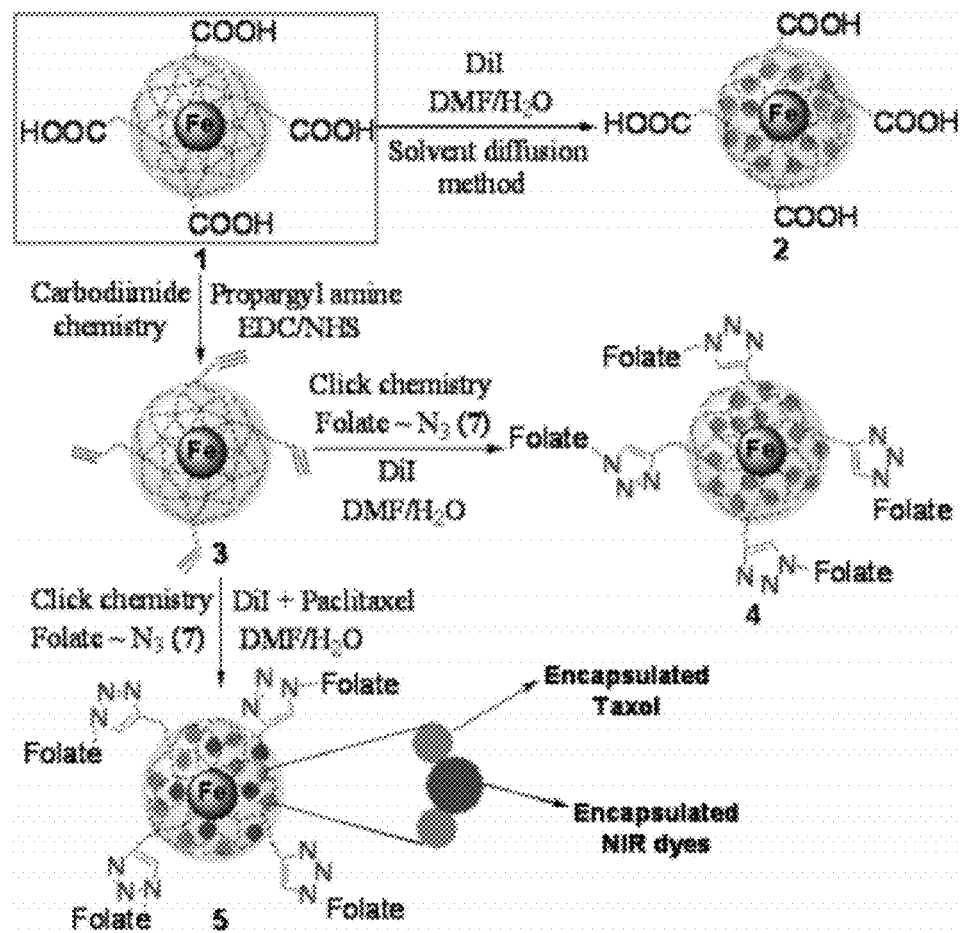
FIG. 1 is a schematic representation of the synthesis of theranostics and multimodal IONPs according to an embodiment of the present invention; click chemistry and carbodiimide chemistry have been used for the synthesis of a library of functional IONPs; NIR dyes and paclitaxel coencapsulated IONPs were prepared in water using the modified solvent diffusion method detailed below.

The present invention will now be described more fully hereinafter with reference to the accompanying drawings, in which preferred embodiments of the invention are shown. Unless otherwise defined, all technical and scientific terms used herein have the same meaning as commonly understood by one of ordinary skill in the art to which this invention pertains. Although methods and materials similar or equivalent to those described herein can be used in the practice or testing of the present invention, suitable methods and materials are described below. Any publications, patent applications, patents, or other references mentioned herein are incorporated by reference in their entirety. In case of conflict, the present specification, including any definitions, will control. In addition, the materials, methods and examples given are illustrative in nature only and not intended to be limiting. Accordingly, this invention may be embodied in different forms and should not be construed as limited to the illustrated embodiments set forth herein. Rather, these illustrated embodiments are provided so that this disclosure will be thorough and complete, and will fully convey the scope of the invention to those skilled in the art. Other features and advantages of the invention will be apparent from the following detailed description, and from the claims.

Materials and Methods:

Iron salts: $FeCl_2 \cdot 4H_2O$ and $FeCl_3 \cdot 6H_2O$, ammonium hydroxide, hydrochloric acid, folic acid, DMF, 3-(4,5-Dimethylthiazol-2-yl)-2,5-diphenyltetrazolium bromide (MTT), esterase (from porcine liver, 16.5 mg protein/mL of Biuret, 177 units/mg of protein), N-hydroxysuccinimide (NHS), polyacrylic acid and other chemicals were purchased from Sigma-Aldrich. Dialkylcarbocyanine fluorescent dyes (DiI—D282 and DiR—D12731) and 4', 6-diamidino-2-phenylindole (DAPI—D1306) were purchased from Invitrogen, EDC (1-Ethyl-3-[3-dimethylaminopropyl]carbodiimide hydrochloride) was obtained from Pierce Biotechnology. The human lung carcinoma A549 (CCL-185) and cardiomyocyte (H9c2) cell lines were obtained from ATCC. Dialysis membranes were obtained from Spectrum Laboratories. Nitrogen purged DI water was used in the synthesis.

Instrumentation: Infrared spectra were recorded on a PerkinElmer Spectrum 100 FT-IR spectrometer. UV/Vis spectra were recorded using CARY 300 Bio UV/Vis spectrophotometer. Fluorescence spectra were recorded on a NanoLog Horiba JobinYvon spectrophotometer. NMR spectrum was recorded on a MERCURY 300 MHz spectrometer using the TMS/solvent signal as an internal reference. Dynamic light scattering (DLS) studies were done using a PDDLS/CoolBatch 40T instrument using Precision Deconvolve 32 software. High throughput absorbance readings for MTT assays were done using a BIO-TEK Synergy HT multi-detection microplate reader. The core size and morphology of the nanoparticles were characterized by using high resolution transmission electron microscopy (HRTEM, FEI Technai F30). Overall surface charge (zeta potential) of IONP was measured using Zetasizer Nano ZS from Malvern Instruments. Transverse (T2) proton relaxation times measurements were done using a Bruker Minispec mq20 NMR analyzer operating at a magnetic field of 0.47 T and at 37° C. Fluorescent images of nanoparticles in solution were performed using a Maestro CIRL optical imaging scanner. Magnetic resonance images of nanoparticles in solution were performed using a 4.7 T Bruker horizontal bore small animal MR scanner.

Synthesis of Azide-Functionalized Folic Acid (7, Folate~N3) by Carbodiimide Chemistry

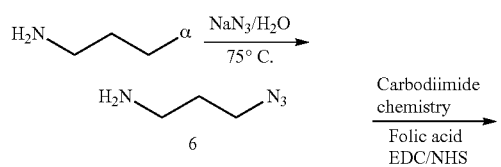

Formula 1

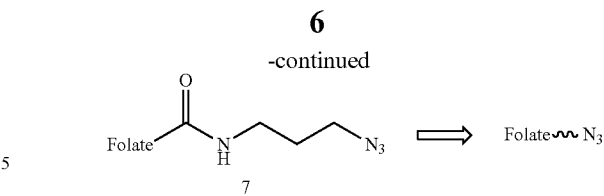

The scheme for synthesis of azido-folic acid (7) from chloropropyl amine is shown above.

Synthesis of Aminopropylazide (6): In a 100 mL round bottom flask, chloropropyl amine (7.0 g, 75.26 mmol) and sodium azide (14.23 g, 225.81 mmol) were added to 40 mL of distilled water and heated at 80° C. for 20 h. The reaction mixture was concentrated in a rotary evaporator at high vacuum, 2 g of KOH were added and the product was extracted using diethyl ether.

Subsequently, the reaction mixture was dried over anhydrous sodium sulphate and concentrated. Finally, the product was purified via flash column chromatography using 4% ethyl acetate in petrolium ether as an eluant. Yield: 5.1 g (68%). 1H NMR (300 MHz, CDCl$_3$, d ppm): 1.26 (bs, 2H), 1.81 (m, 2H), 2.80 (t, 2H), 3.38 (t, 2H). FT-IR(CHCl$_3$): 3307, 2941, 2089, 1663, 1433, 1370, 1259, 1242, 1075, 1026, 818, 760 cm$^{-1}$.

Synthesis of azide-functionalized folic acid (7): To a solution of folic acid (0.05 g, 0.12 mmol) in DMSO (2 mL), EDC (0.021 g, 0.11 mmol) and NHS (0.013 g, 0.11 mmol) in 0.5 mL MES buffer (pH=5.0) were added and then incubated at room temperature for 3 minutes. To this resulting reaction mixture was added drop-wise ethylenediamine (0.007 g, 0.11 mmol) in 0.25 mL of PBS (pH=7.4) and then incubated for 3 h at room temperature. The reaction mixture was centrifuged and washed to remove excess starting materials. The azide-functionalized folic acid was dissolved in 1 mL of DMF until further use. Yield: 0.05 g (86%). The presence of a band at 2097 cm$^{-1}$ in the IR spectrum and a UV absorbance shoulder at 354 nm confirmed the formation of azide-functionalized folic acid. 1H NMR (400 MHz, DMSO-d6, d ppm): 1.61 (m, 2H), 1.65 (m, 2H), 1.90 (m, 2H), 2.19 (t, 2H), 2.78 (t, 2H), 4.18 (q, 1H), 4.21 (d, 2H), 6.62 (d, 2H), 7.59 (d, 2H), 8.58 (s, 1H). FT-IR: 3024, 2097, 1685, 1603, 1492, 1375, 1291, 1248, 1180, 1122, 1062, 950, 844, 755, 696 cm$^{-1}$.

Figure 6:
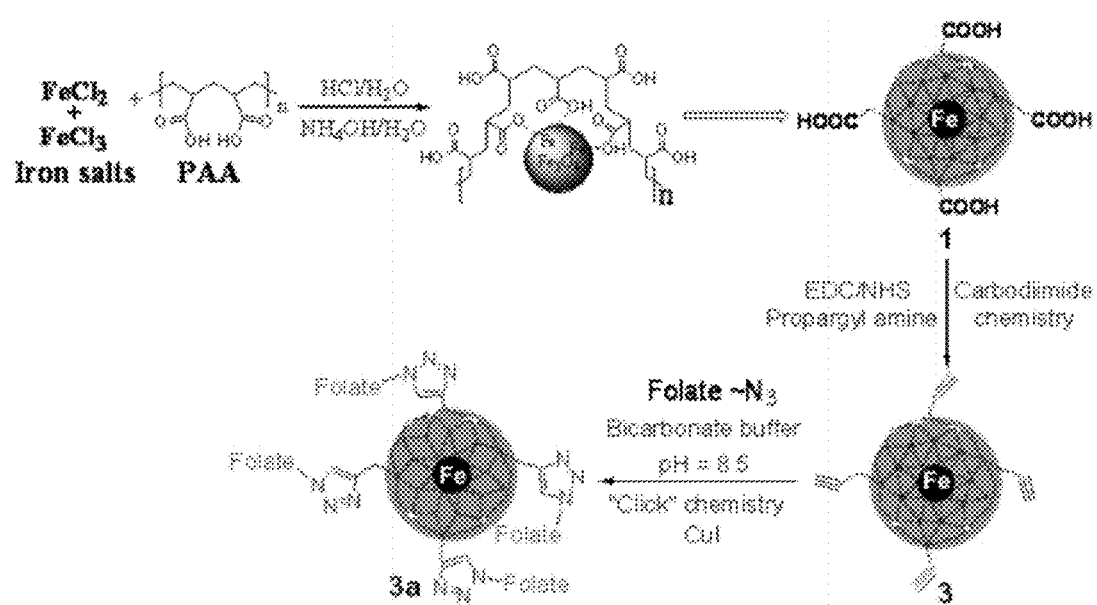
FIG. 6 illustrates synthesis of folate conjugated PAA-IONPs using carbodiimide chemistry and "click" chemistry.
Figure 8:
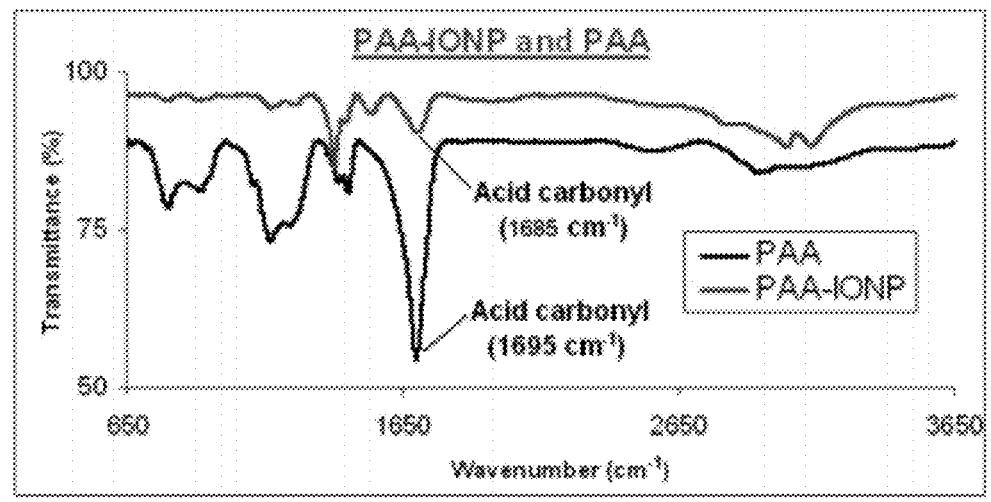
FIG. 8 is an FT-IR spectroscopic analysis of the synthesized IONPs (1, PAA-IONP, red line) and polyacrylic acid (PAA, black line); presence of the band at 1685 cm$^{-1}$ in 1 confirms the presence of a PAA coating in the IONPs.

Synthesis of PAA-IONPs (1): For the water-based, step-wise synthesis of polyacrylic acid-coated iron oxide nanoparticles (PAA-IONPs), three solutions were prepared; an iron salt solution [0.62 g of $FeCl_3 \cdot 6H_2O$ and 0.32 g of $FeCl_2 \cdot 4H2O$ in dilute HCl solution (100 µL of 12 N HCl in 2.0 mL $H_2O$)]; an alkaline solution [1.8 mL of 30% $NH_4OH$ solution in 15 mL of $N_2$ purged DI water]; and a stabilizing agent solution [820 mg of polyacrylic acid in 5 mL of DI water]. To synthesize the PAA-IONP, the iron salt solution was added to the alkaline solution under vigorous stirring. The resulting dark suspension of iron oxide nanoparticles was stirred for approximately 30 seconds before addition of the stabilizing agent solution and stirred for 1 h. The resulting suspension of PAA-IONPs was then centrifuged at 4000 rpm for 30 minutes and the supernatant was washed three times with DI water to get rid of free polyacrylic acid and other unreacted reagents using an Amicon 8200 cell (Millipore ultra-filtration membrane YM—30 k). Finally, the PAA-IONP suspension was purified using magnetic column, washed with phosphate buffer saline (pH=7.4) and concentrated using the Amicon 8200 cell system. The iron concentration and magnetic relaxation of the PAA-IONPs was determined as previously reported [Josephson et. al. Bioconjugate Chem 1999, 10, 186-191]. The successful coating of the IONPs with PAA was confirmed by the presence of a negative zeta-potential ($\zeta=-48$ mV) and the characteristic acid carbonyl bands on the FT-IR spectroscopic analysis of the nanoparticles (FIGS. 6 and 8).

Figure 9:
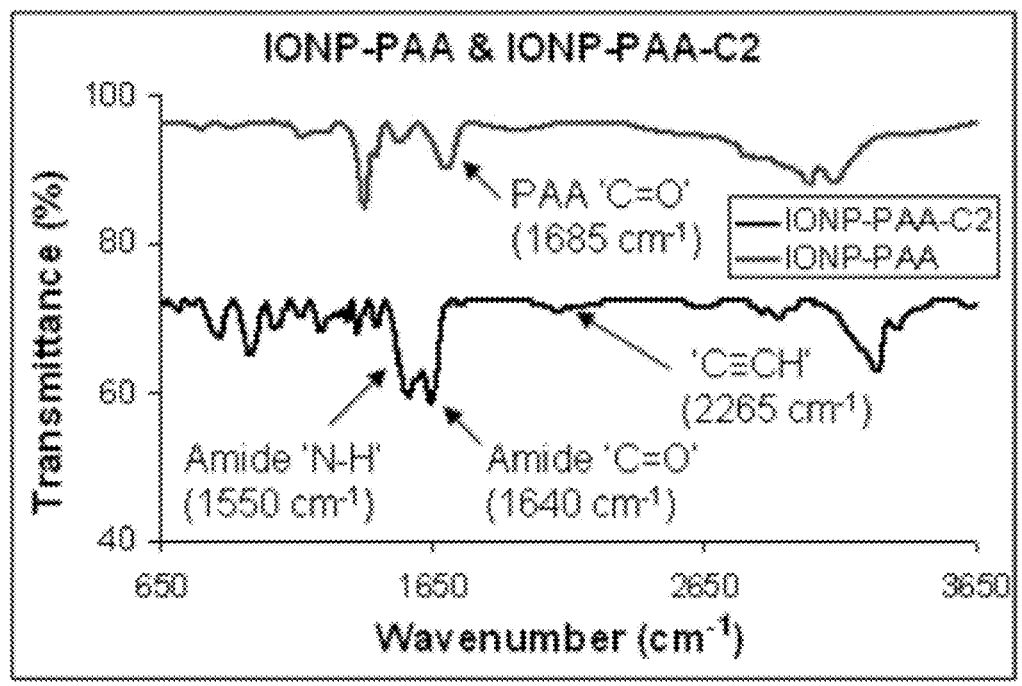
FIG. 9 are FT-IR spectra of propargylated nanoparticles (3, IONP-PAA-C2, black line) and carboxylated IONP (1, IONP-PAA, red line); presence of a weak band at 2265 cm$^{-1}$ confirms the presence of propargyl groups in IONPs 3.

Synthesis of propargylated IONPs (3): Carbodiimide chemistry. To a suspension of PAA-IONP (1) (45 mg Fe) in MES buffer (26 mL, pH=6), a solution of EDC (87 mg, 10 mmol) and NHS (52 mg, 10 mmol) in MES buffer (2 mL) was added and incubated for 3 minutes. To the resulting reaction mixture, propargyl amine (25 mg, 10 mmol) in DMF (0.5 mL) was added drop-wise and incubated for 5 h at room temperature. The resulting reaction mixture was then purified using magnetic column and then using amicon 8200 cell (Millipore ultra-filtration membrane YM—30 k) to get rid of unreacted propargyl chloride and other unreacted reagents and kept in PBS at 4° C. FT-IR data analysis (FIG. 9) confirms the completion and success of the conjugation.

Figure 10:
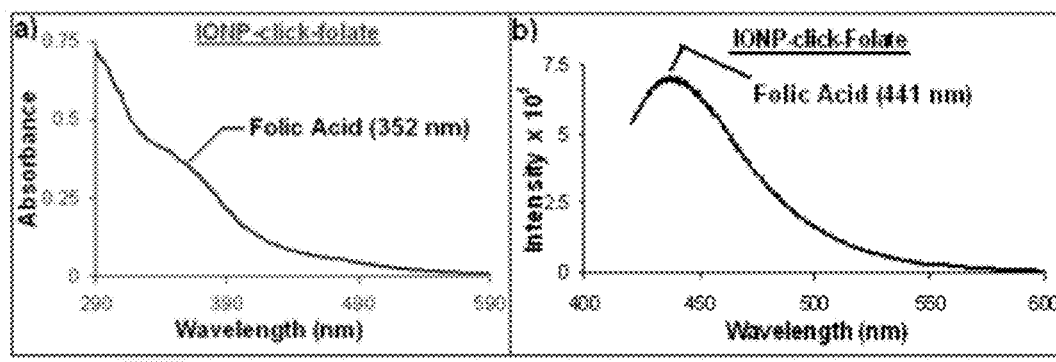
FIG. 10 shows spectrophotometric characterizations of the folate-conjugated PAA-IONPs (3a); a) UV/Vis spectrum of 3a showing absorbance at 352 nm, indicating the presence of folic acid on the iron oxide nanoparticles; b) fluorescence emission spectrum (a.u.) of 3a showing the characteristic fluorescent emission at 441 nm and confirming the presence of folic acid on the nanoparticles.
Figure 12:
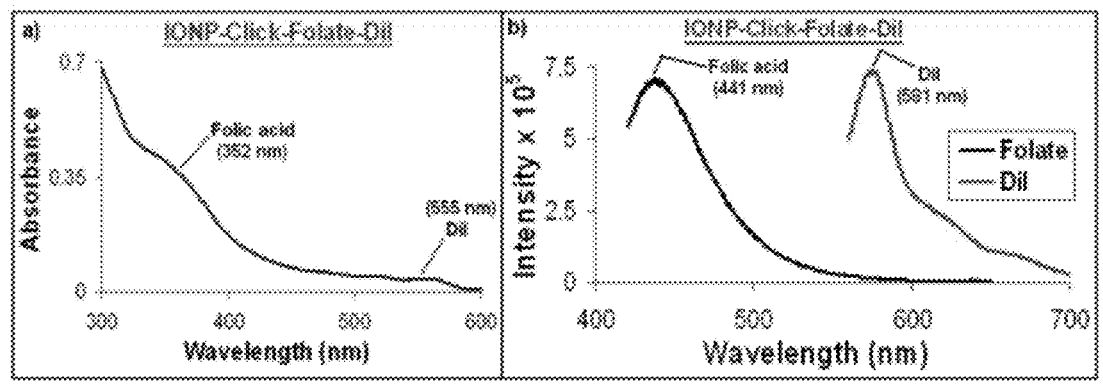
FIG. 12 presents spectrophotometric characterizations of the DiI encapsulated folate clicked IONPs (4); a) UV/Vis spectrum showing absorbance at 352 nm and 555 nm indicating the presence of folic acid and DiI dye, respectively; b) Fluorescence emission spectrum (a.u.) showing intensity maximum at 441 nm and 581 nm confirmed for the "click" chemistry with folic acid and effective encapsulation of DiI dye; similar results were obtained for paclitaxel and DiI encapsulated folate conjugated IONPs.

General procedure for dye-encapsulated functional IONPs (2, 4): Modified solvent diffusion method. To a suspension of IONPs (4.5 mL, [Fe]=1.1 mg/mL) in PBS, a solution of the corresponding dialkylcarbocyanine fluorescent dyes (DiI or DiR, 0.1 µg/µL) in DMF was added drop-wise at room temperature with continuous stirring at 1000 rpm. The resulting dye-encapsulated IONPs were purified using a magnetic column and then dialyzed (using 6-8 K molecular weight cut off dialysis bag) three times against deionized water and finally against phosphate buffered saline solution. The successful encapsulation of the corresponding dye (DiI or DiR) on the PAA-IONPs was confirmed by UV/Vis spectrophotometric measurements (FIG. 10*a-b*). In addition, when these nanoparticles were functionalized with folate, the presence of both folate and dye encapsulated groups were assessed by UV/Vis (FIG. 12*a*) and fluorescence (FIG. 12*b*) spectrometry.

Figure 13:
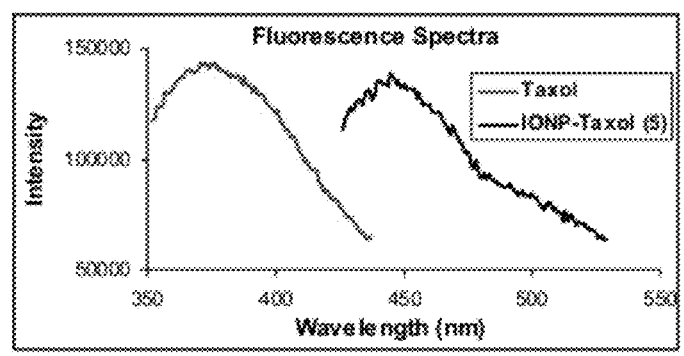
FIG. 13 provides fluorescence emission spectra (a.u.) showing intensity maximum at 445 nm for Taxol® encapsulated IONPs (5) and 375 nm for free Taxol®, confirming the presence of the drug inside the PAA polymer coating of the iron oxide nanoparticles.

Procedure for co-encapsulation of Paclitaxel and Oil into IONPs (5): A solution containing paclitaxel (5 µL, 0.05 µg/µL) and DiI dye (5 µL, 0.1 µg/µL) in 500 µL DMF was used and the same modified solvent diffusion method was followed as described above. The presence of Taxol® in the IONPs (5) was confirmed by using fluorescence spectrophotometer (FIG. 13).

Synthesis of 3a: Folate conjugation using Click chemistry. To a suspension of propargylated IONPs 3 (13 mg Fe) in bicarbonate buffer (pH=8.5), a catalytic amount of CuI (0.06 µg, 3×10-10 mmol) were added for a total volume of 125 µL of bicarbonate buffer and vortexed for 30 seconds. Then, a solution of azide-functionalized folic acid (7, Formula I—above, 0.003 g, 6×10-2 mmol) in DMSO was added and incubated at room temperature for 12 h. The final reaction mixture was purified by using magnetic column and by dialysis using 6-8 K molecular weight cut off dialysis bag, against deionized water first and a finally with a phosphate buffered saline (PBS) solution. The purified functional IONPs were stored at 4° C. until further use. The successful conjugation of folic acid with PAA-IONPs was confirmed by UV/Vis (FIG. 10*a*) and fluorescence (FIG. 10*b*) spectrophotometric measurements.

Cell culture and cell viability studies: MTT assay. The lung carcinoma cells (A549) and cardiomyocytes (H9c2) were obtained from ATCC, USA. Lung carcinomas were grown in Kaighn's modification of Ham's F12 medium (F12K—Cellgro), supplemented with 5% fetal bovine serum (Heat-inactivated FBS—Cellgro), L-glutamine, streptomycin, amphotericin B, and sodium bicarbonate. The cells were maintained at 37° C., 5% CO2 in a humidified incubator. Cardiomyocyte cells were grown in Eagle's Minimal Essential medium supplemented with 10% fetal bovine serum, sodium pyruvate, L-glutamine, penicillin, streptomycin, amphotericin B and sodium bicarbonate. For MTT assay, lung carcinoma and cardiomyocyte cells (2,500 cells/well) were seeded in 96-well plates, and were incubated with the IONPs for 3 h at 37° C. Then, each well was washed three times with 1×PBS and treated with 20 µL MTT (5 µg/µl, 3-(4,5-dimethylthiazol-2-yl)-2,5-diphenyltetrazolium bromide, Sigma-Aldrich) for 2 h. The resulting formazan crystals were dissolved in acidified isopropanol (0.1 N HCl) and the absorbance was recorded at 570 nm and 750 nm (background), using a Synergy HT multi-detection microplate reader (Biotek). These experiments were performed in triplicate.

Cellular internalization: Confocal Microscopy and IVIS experiments. A Zeiss LSM 510 confocal and Zeiss Axiovert 200 epifluorescence microscopes were used to assess the uptake of folate-derivatized IONPs by the human lung carcinoma (A549) cell line. Specifically, A549 cells (10,000) were incubated with the corresponding IONPs preparation (1.1 mg/mL) for 3 h in a humidified incubator (37° C., 5% $CO_2$). Subsequently, the cells were thoroughly washed three times with 1×PBS and fixed with 10% formalin solution. Nuclear staining with DAPI was performed as recommended by the supplier. Then, multiple confocal images were obtained, achieving a representative view of the cell-IONPs interaction. For the IVIS analysis, 10,000 lung carcinoma cells were incubated for 3 h with the corresponding IONPs and the supernatant was collected in Eppendorf Tubes®. Cells were thoroughly washed with 1×PBS and detached them, as stated above. The resulting pellets were resuspended in 1 mL culture media. All Eppendorf Tubes® were examined simultaneously on a Xenogen® IVIS system, using the ICG filter for DiR dye. All experiments were performed in triplicate.

In Vitro drug/dye release: The in vitro drug/dye release studies were carried out using a dynamic dialysis technique at 37° C. Briefly, 100 µL of IONPs (5) are incubated with a porcine liver esterase (20 µL) inside a dialysis bag (MWCO 6000-8000), which is then placed in a PBS solution (pH 7.4). The amount of guest (dye or drug) molecules released from the nanoparticle into the PBS solution was determined at regular time intervals by taking 1-mL aliquots from the PBS solution and measuring the fluorescence intensity at 581 nm for DiI and 375 nm for Taxol®. The concentration of the either dye or drug was calculated using a standard calibration curve. The cumulative fraction of release versus time was calculated using the following equation:

$$\text{Cumulative release}(\%)=[\text{guest}]t/[\text{guest}]\text{total}\times 100$$

Where [guest]t is the amount of guest released at time t, [guest]total is the total guest present in the guest encapsulated IONPs.

TABLE 1

| IONPs | 1 | 2 | 3 | 4 | 5 | Time |
|---|---|---|---|---|---|---|
| $R_2$ | 206 ± 2 | 202 ± 3 | 207 ± 2 | 204 ± 3 | 203 ± 5 | 15 |
| D | 86 | 90 | 87 | 94 | 96 | Days |
| (PDI) | (0.89) ± 1 | (0.87) ± 2 | (0.89) ± 1 | (0.87) ± 3 | (0.91) ± 3 | |
| $R_2$ | 206 ± 1 | 201 ± 2 | 207 ± 3 | 204 ± 2 | 204 ± 4 | 1 |
| D | 86 | 91 | 87 | 94 | 96 | Month |
| (PDI) | (0.89) ± 2 | (0.88) ± 3 | (0.92) ± 2 | (0.88) ± 3 | (0.90) ± 4 | |
| $R_2$ | 208 ± 3 | 202 ± 4 | 208 ± 2 | 203 ± 3 | 205 ± 5 | 3 |
| D | 88 | 91 | 89 | 95 | 98 | Months |
| (PDI) | (0.91) ± 2 | (0.90) ± 4 | (0.88) ± 2 | (0.91) ± 4 | (0.91) ± 4 | |
| $R_2$ | 210 ± 4 | 204 ± 4 | 207 ± 3 | 205 ± 4 | 208 ± 5 | 6 |
| D | 87 | 92 | 88 | 96 | 100 | Months |
| (PDI) | (0.95) ± 4 | (0.92) ± 5 | (0.91) ± 4 | (0.89) ± 4 | (0.88) ± 5 | |

Table 1 shows Magnetic relaxivity (R2, $s^{-1}$ $mM^{-1}$), Hydrodynamic diameter (D, m) and Polydispersity index (PDI) of all the functional iron oxide nanoparticles (IONPs) over the period of time, showing the stability of the functional IONPs (1-5) in aqueous buffered solution.

Proof of Folate Receptor Mediated Internalization: Confocal Microscopy and IVIS Experiments.

A Zeiss LSM 510 confocal fluorescence microscope was used to assess the uptake of folate-derivatized IONPs by the human lung carcinoma (A549) cell line. Specifically, A549 cells (10,000) were incubated with the corresponding IONPs preparation (1.1 mg/mL) for 3 h in a humidified incubator (37° C., 5% $CO_2$).

Figure 15:
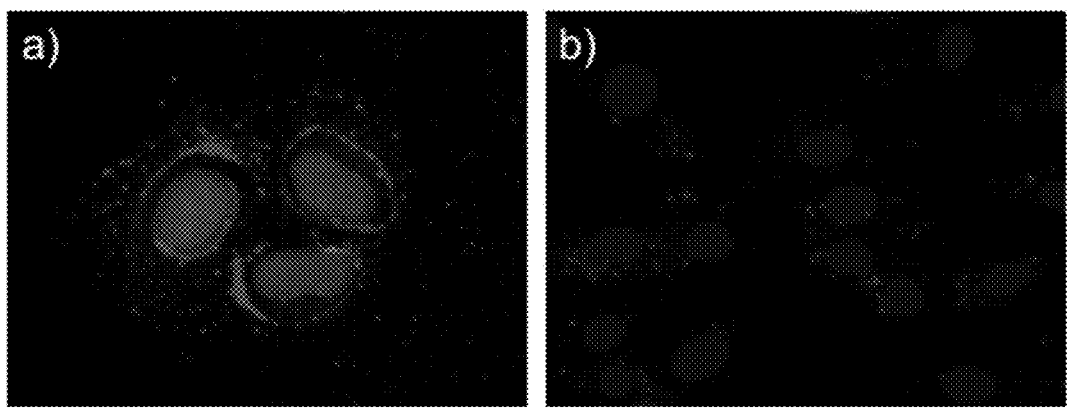
FIG. 15 shows confocal images of a) lung carcinoma A549 cells pre-incubated (saturated, no free folate receptor) with free folic acid (100 µL, 10 mg/mL) and then incubated with folate-IONPs (4, 50 µL, 1.1 mg/mL) and free folic acid (50 µL, 10 mg/mL); b) cardiomyocyte cells (H9c2, no folate receptor) incubated with folate-IONPs (4, 50 µL, 1.1 mg/mL); no internalization was observed due to absence of free folate receptors (a, A549) or absence of folate receptors (b, H9c2); these observations confirmed the targeting capability and receptor mediated endocytosis of our theranostic IONPs; cells incubated for 3 h with functional IONPs 4 and the nuclei were stained with DAPI (blue)

Subsequently, the cells were thoroughly washed three times with 1×PBS and fixed with 10% formalin solution. Nuclear staining with DAPI was performed as recommended by the supplier. Then, multiple confocal images were obtained, achieving a representative view of the cell-IONPs interaction (FIG. 15).

To prove that internalization was mediated by the folate receptor, A549 cells were pre-incubated with free folate (to saturate the folate receptor) and then treated with the folate derivatized IONP (4). Results show no significant internalization of the nanoparticles (FIG. 15a). Furthermore, no internalization of 4 was observed when H9c2, a cardiomyocyte cell line that does not express the folate receptor, was used (FIG. 15b).

Fluorescence Imaging of Multimodal Nanoparticles in Solution.

To assess the potential application of the multimodal nanoparticles 4, in vivo, encapsulating either DiI or DiR, (4-DiI or 4-DiR), a Maestro CIRL (Woburn, Mass.) was used. Furthermore, a 1:1 mixture of the DiI and DiR nanoparticles was prepared and image. Results show the capability of imaging both nanoparticles simultaneously.

Discussion

Specifically, our synthetic procedure differs from the previously reported methods in that the polymer is not present during the initial nucleation process.[6-8] Instead, the polyacrylic acid is added at a later stage. This "step-wise" process, as opposed to the "in-situ" process, allows for the formation of stable, disperse and highly crystalline superparamagnetic iron oxide nanocrystals coated with PAA, (See 1, FIG. 1). The successful coating with PAA was confirmed by the presence of a negative zeta-potential ($\zeta$=−48 mV) and via FT-IR analysis (See FIG. 8).

We then hypothesized whether a hydrophobic dye could be encapsulated within the hydrophobic pockets in the PAA coating, generating multimodal IONPs with dual magnetic and fluorescent properties. As a proof-of-principle, we have encapsulated two lipophilic fluorescent dyes (DiI or DiR) (See 2, FIG. 1) using a modified solvent diffusion method.[9] These dialkylcarbocyanine fluorophores (DiI, DiR) are widely used in biomedical applications to label cell membranes and were selected because of their high extinction coefficients (c>125,000 $cm^{-1}$ $M^{-1}$) and high fluorescence in hydrophobic environments.[9] The long chain dialkylcarbocyanine dye, DiR, is of particular importance since it has an excitation/emission near the infrared region (751/780), it is suitable for in vivo imaging.

Next, the IONP 1 was functionalized to yield a propargylated nanoparticle (See 3, FIG. 1), which was later used to generate a multimodal folate-derivatized nanoparticle (See 4, FIG. 1) via highly selective 1,3-dipolar cycloaddition reaction ("click" chemistry).[10] Thus, the water-soluble carbodiimide EDC [11], [1-ethyl-3-(3-dimethylaminopropyl) carbodiimide hydrochloride] was utilized to prepare the propargylated IONP (See 3, FIG. 1), which is an important synthon for the synthesis of a library of functional IONPs via "click" chemistry. The presence of a weak 'C≡C' band at 2265 $cm^{-1}$ in the FT-IR spectrum of these nanoparticles confirmed the presence of a propargyl (triple bond) group (See FIG. 9).

Figure 11:
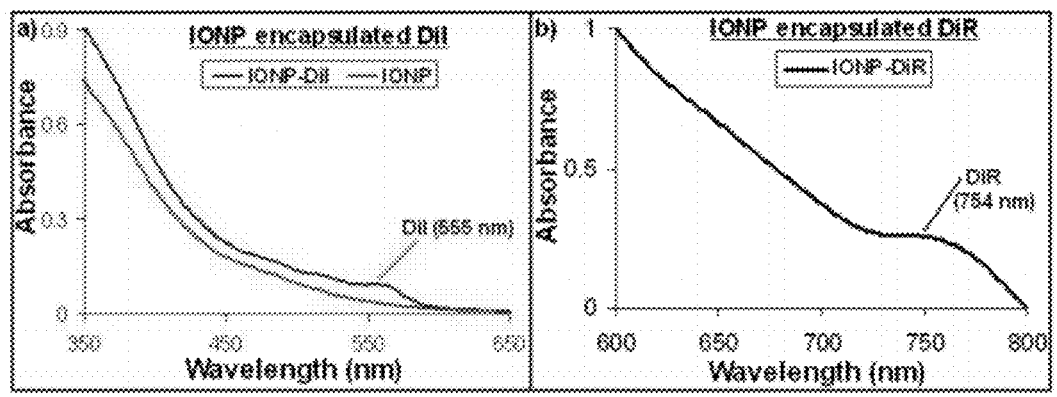
FIG. 11 depicts UV/Vis spectra of a) DiI encapsulated IONPs (2) and b) corresponding DiR encapsulated IONPs (2-DiR) showing the presence of encapsulated DiI (555 nm) and DiR (754 nm) inside the PAA coating of IONPs.

As a model system, we conjugated the nanoparticle 3, illustrated in FIG. 1, with an azide-functionalized folic acid analog (See also FIG. 6 and synthesis of azide-functionalized folic acid, above) via "click" chemistry. The resulting folate-decorated IONPs are soluble in aqueous media and can encapsulate lipophilic fluorescent dyes. The presence of folic acid and dye in these multimodal folate-derivatized nanoparticles (See 4, FIG. 1) was confirmed through various spectrophotometric studies (See FIGS. 10-12). Furthermore, a hydrophobic anti-cancer drug (paclitaxel, a.k.a. Taxol®) was encapsulated to yield a theranostic (therapeutic and diagnostic) nanoparticle with dual imaging and therapeutic properties (See 5, FIG. 1). These functional IONPs (1-5) were highly stable in aqueous solutions, as their magnetic relaxivity (R2), hydrodynamic diameter (D) and polydispersity index (PDI) remained unaffected over a long period of time (See Table 3). Therefore, the versatility of our method allows the generation of a small library of multifunctional, multimodal and targetable IONPs.

Figure 2:
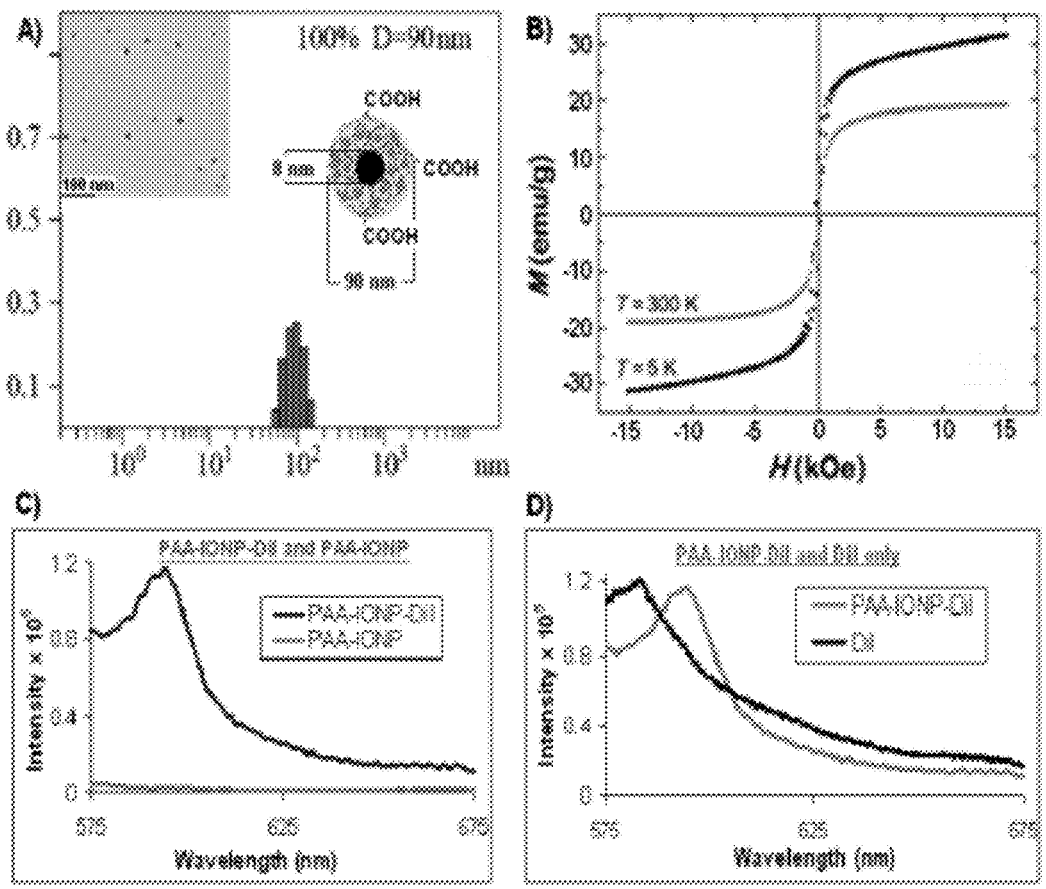
FIG. 2 shows the characterization of multimodal nanoparticles 2 (PAA-IONP-DiI); A) determination of hydrodynamic diameter of the IONPs through Dynamic Light Scattering (DLS), Inset: Transmission Electron Microscope (TEM) image of the corresponding nanoparticles (scale bar 100 nm.); B) magnetic hysteresis loops at 300 and 5 K, showing nanoparticles are superparamagnetic; C) fluorescence emission spectra (in PBS buffer) of DiI dye encapsulated IONPs 2 and that of 1 without any dye; D) fluorescence emission spectra of 2 and that of free non-encapsulated DiI in solution.
Figure 7:
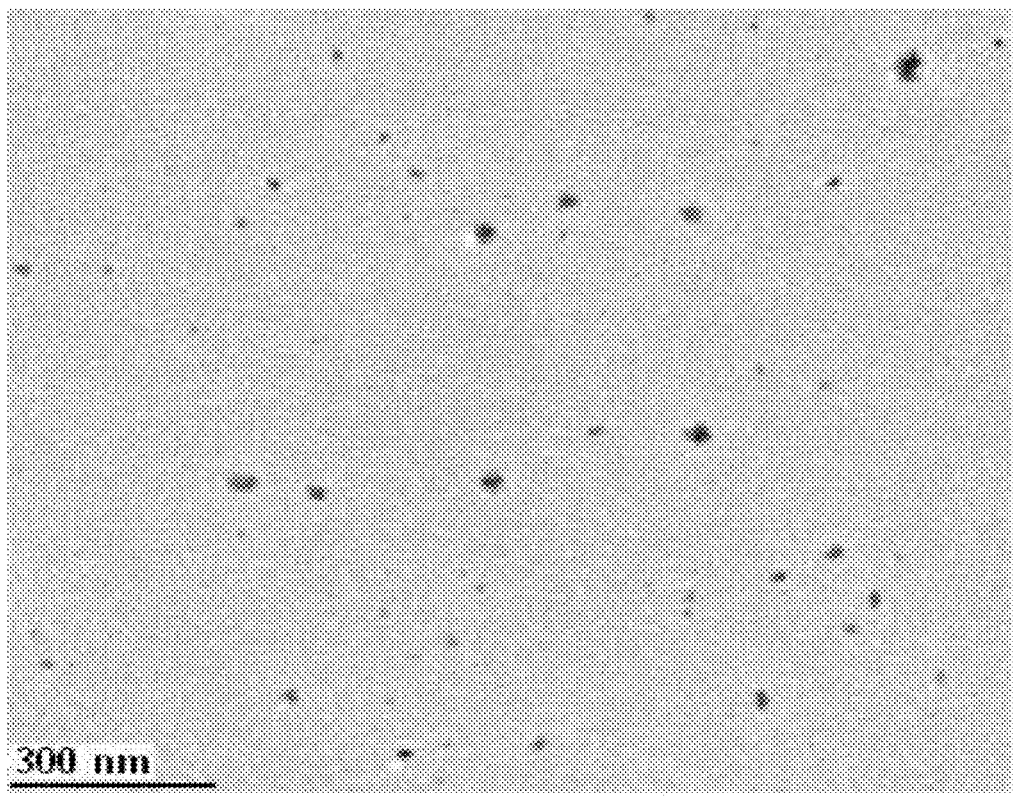
FIG. 7 shows a High Resolution Transmission Electron Microscope (HR-TEM) image of the polyacrylic acid coated iron oxide nanoparticles (PAA-IONPs, 2); scale bar 300 nm.

Dynamic light scattering (DLS) studies of the functional PAA-IONP (2) confirmed the presence of stable and monodispersed nanoparticles with a hydrodynamic diameter of 90 nm (FIG. 2A), while TEM experiments revealed an iron oxide core of 8 nm (Inset: FIG. 2A; see also FIG. 7). These measurements suggest the formation of a thick polymeric coating (~40 nm) around the iron oxide core, which plays a key role in the encapsulation of hydrophobic guest molecules. FT-IR analysis further confirmed the presence of the PAA coating and carboxylic acid groups on 1, as well as the corresponding surface propargyl groups on nanoparticle 3 (See FIGS. 8-9). Magnetic hysteresis loops (FIG. 2B) corroborated the superparamagnetic nature of the nanoparticles, while water relaxation measurements using a 0.47T Bruker's Minispec relaxometer indicated the presence of magnetic IONPs with high water relaxation (R1=53 $s^{-1}$ $mM^{-1}$, R2=202 $s^{-1}$ $mM^{-1}$). The incorporation of a hydrophobic dye into 1 was done using a modified solvent diffusion method.[9] Specifically, a solution of DiI in DMF (0.1 μg/μL) was added drop-wise to a stirring aqueous nanoparticle suspension (4.5 mL and [Fe]=1.1 mg/mL). The slow addition of the dye solution allows for the rapid diffusion of DMF into the aqueous medium, causing the dye to become encapsulated in the hydrophobic microdomains of the PAA coating. The presence of an absorption maximum at 555 nm in the UV/Vis spectrum (See FIG. 11a) and a corresponding fluorescence emission peak at 595 nm (FIG. 2C) confirmed the presence of DiI in the nanoparticle. Furthermore, the encapsulation of DiI was confirmed by the presence of a 14 nm red-shift in the fluorescence intensity maximum of the DiI-encapsulating PAA-IONP, as compared to the free DiI (581 nm, FIG. 2D). Similar red-shifts have been previously reported in other systems, indicating an interaction of the fluorescent guest molecule with the electronic environment of the encapsulating pocket.[12] Next, we encapsulated both DiI and Taxol® to the folate-conjugated nanoparticle for dual cellular imaging and targeted cancer therapy. To synthesize such nanoparticle (5), a DMF solution containing DiI (0.1 μg/μL) and Taxol® (0.05 μg/μL) was added to a stirring solution of folate-derivatized PAA-IONPs (See compound 3a in FIG. 6). Since the dye and the drug are hydrophobic, we expected both molecules to become encapsulated. The encapsulation of Taxol® was confirmed through fluorescence spectroscopy (FIG. 13). Furthermore, the amount of dye, folic acid and Taxol® molecules per nanoparticle was calculated, as previously described [13] (Table 2). These dye-encapsulating PAA-IONPs were highly stable in aqueous solutions for more than a year, without significant reduction in the fluorescence emission of the encapsulated dyes. Additionally, no leaching of the encapsulated dye from the nanoparticle occurred, as no precipitation of the dye was observed after prolonged storage in PBS, pH 7.4.

TABLE 2

Determination of magnetic relaxivity (R2), hydrodynamic diameter (D) and polydispersity index (PDI) of functional IONPs immediately after synthesis. Quantitative estimation of amount of dye, folic acid and Taxol ® per iron crystal of the corresponding multifunctional IONPs (1-5).

| IONPs | $R_2$ $s^{-1} mM^{-1}$ | D (PDI) nm | Dye/ IONPs | Folate/ IONPs | Taxol/ IONPs |
|---|---|---|---|---|---|
| 1 | 206 ± 2 | 86 (0.89) ± 1 | — | — | — |
| 2 | 202 ± 3 | 90 (0.87) ± 2 | 31 ± 2 | — | — |
| 3 | 207 ± 2 | 87 (0.89) ± 1 | — | — | — |
| 4 | 204 ± 3 | 94 (0.87) ± 3 | 28 ± 2 | 12 ± 2 | — |
| 5 | 203 ± 5 | 96 (0.91) ± 4 | 19 ± 1 | 12 ± 2 | 11 ± 3 |

Figure 3:
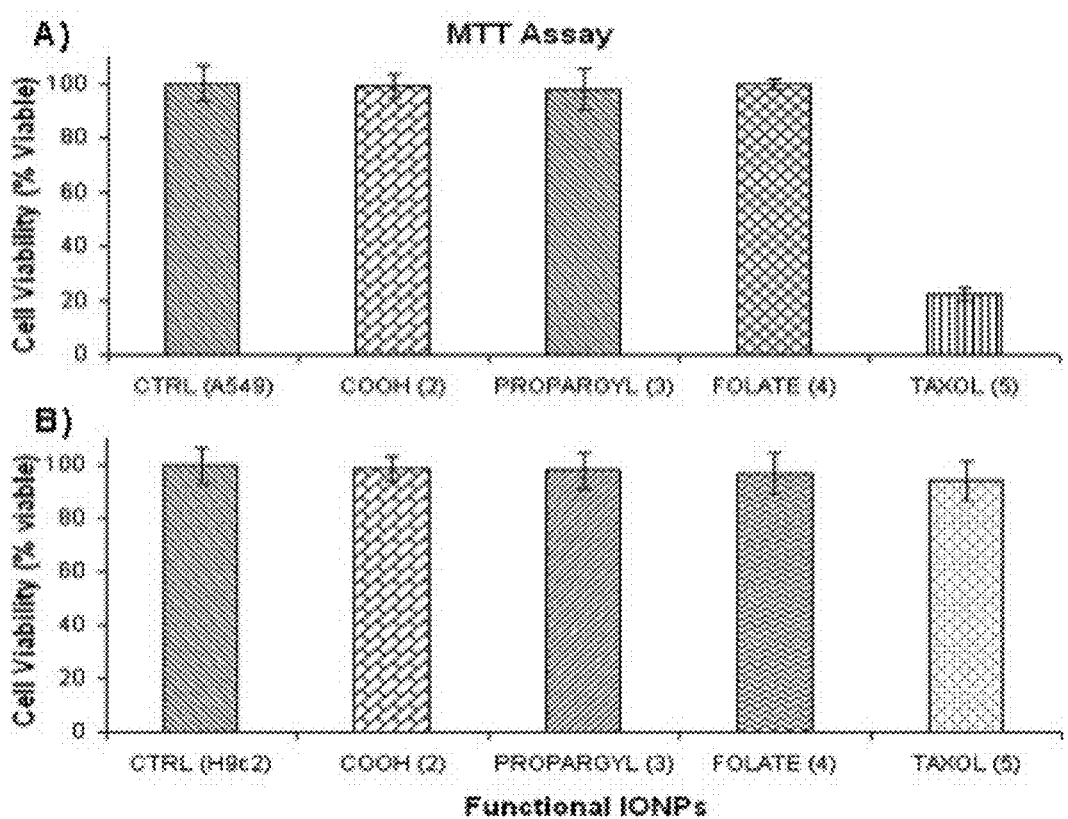
FIG. 3 shows a determination of cytotoxicity of the functional IONPs: carboxylated [COOH (2)], propargylated [PROPARGYL (3)], folate-conjugated [FOLATE (4)] and Taxol-carrying [TAXOL (5)]; control (CTRL) cells: A) Lung carcinoma cells (A549) and B) Cardiomyocyte cells (H9c2) were treated with PBS; average values of four measurements are depicted±standard error.

To evaluate the potential biomedical applications of the DiI-encapsulating IONPs (2, 3, 4 and 5, 1.1 mg/mL), we assessed their potential cytotoxicity, via the MTT assay (FIG. 3). Therefore, we examined the in vitro differential cytotoxicity of carboxylated (COOH, 2), propargylated (PROPARGYL, 3), folate-decorated (FOLATE, 4), folate-decorated and taxol-encapsulating IONPs (TAXOL®, 5), using lung carcinoma (A549, 2,500 cells/well) (FIG. 2A) and cardiomyocyte cell lines (H9c2, 2,500 cells/well) (FIG. 2B). Carboxylated, propargylated and folate-conjugated IONPs exhibited nominal cytotoxicity (less than 3% compared to the control) towards both cell lines after a 3 h incubation. On the other hand, incubation with the folate-decorated and taxol-carrying IONPs (5) resulted in an 80% reduction in the viability of the lung carcinoma (A549) cell line. In contrast, no significant reduction in cell viability was observed when cardiomyocytes (H9c2) which do not overexpress the folate receptor[14] were incubated with 5. These results demonstrate that nanoparticles 1-4 were not toxic to either A549 or H9c2 cells, hence these nanoparticles can be used as effective multimodal imaging agents. However, as IONP 5 was only cytotoxic to cancer cells (A549) that overexpress folate receptor,[15,16] it can be utilized as a potential targeted multifunctional (imaging and therapeutic) nanoagent for the treatment of folate-receptor-expressing tumors.

Figure 4:
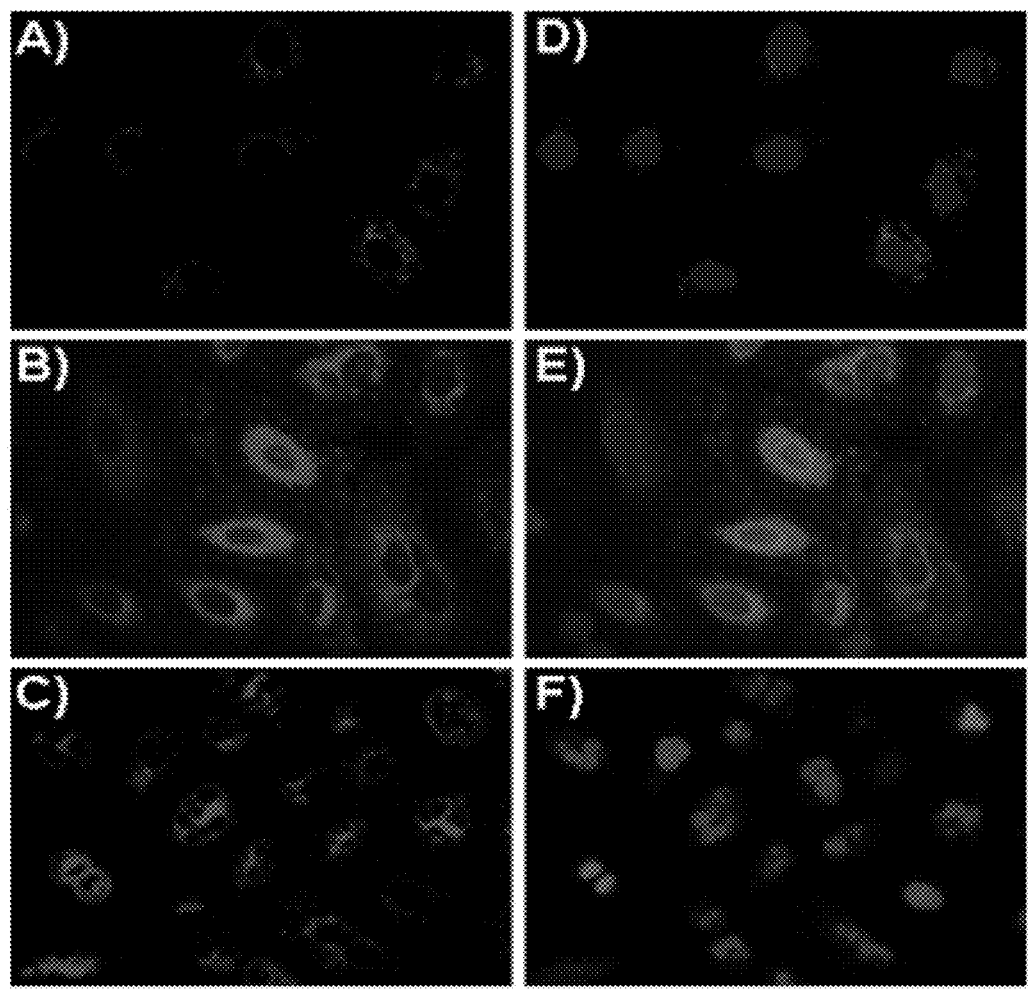
FIG. 4 depicts an assessment of IONPs' cellular uptake via confocal laser-scanning microscopy using lung carcinoma A549 cells; A) no internalization was observed in cells treated with carboxylated IONPs (2), as no DiI fluorescence was observed in the cytoplasm; B) enhanced internalization was observed upon incubation with the folate-immobilized IONPs (4); C) Taxol® and DiI co-encapsulated folate-functionalized IONPs (5) induced cell death; (D-F) corresponding merged confocal images of the functional IONPs treated cells with their nucleus stained with DAPI (blue)

To further explore the potential biomedical applications of the synthesized functional PAA-IONPs, we evaluated the selective uptake of the folate-functionalized nanoparticle (4) by A549 lung cancer cells, as these cells overexpress the folate receptor. In these experiments, carboxylated (2) or folate-conjugated (4) nanoparticles (1.1 mg/mL) were incubated with A549 cells (10, 000 cells) for 3 h, washed to remove non-internalized nanoparticles and visualized via confocal microscopy. Results showed no internalization of the carboxylated nanoparticle (2) as expected (FIG. 4A, 4D). However, significant internalization of the folate-conjugated nanoparticle (4) was indicated by the presence of intense fluorescence in the cytoplasm of the cells (FIG. 4B, 4E).

Figure 14:
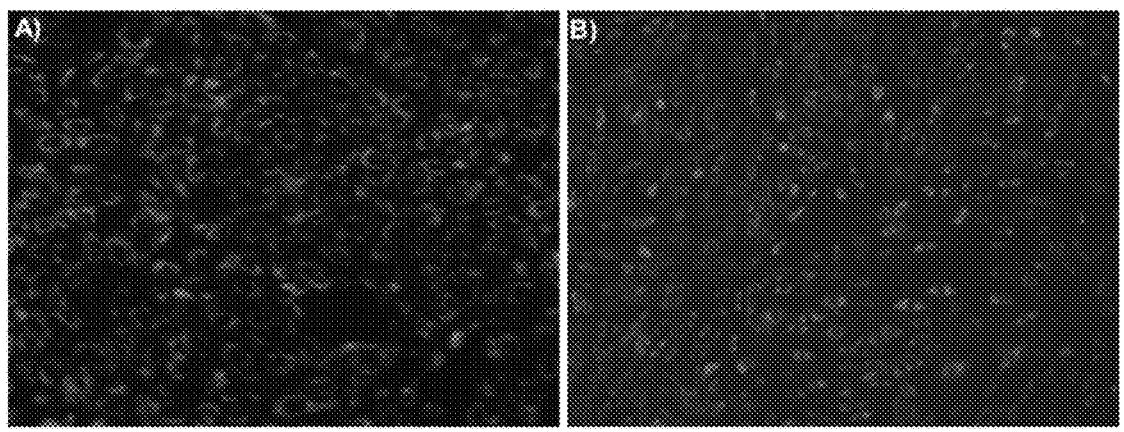
FIG. 14 depicts epifluorescence images of A) live and B) fixed lung carcinoma cells (A549) after incubation of folate-decorated IONPs (4) for 3 h; cell internalization (A549) and cytoplasmic localization is observed either in live or fixed cells; similar results were observed in the case of non-cancerous cell (cardiomyocytes) lines; nucleus stained with DAPI (blue color)

These results were also observed in experiments performed using live (non-fixed) A549 cells, where internalization of the folate-decorated IONPs (4) was monitored through fluorescence microscopy (See FIG. 14). The enhanced cellular uptake of the folate-decorated nanoparticle (4) in A549 cells may have been attributed to folate-receptor mediated internalization. As internalization of 4 was nominal in A549 cells pre-incubated with free folate and in studies using the H9c2 cardiomyocyte cell line (FIG. 15), we corroborated the receptor-mediated internalization of our folate-decorated IONPs (4). Next, we investigated the cellular uptake of a multifunctional folate-conjugated nanoparticle (5) with dual imaging and targeted cancer therapeutic properties. When these IONPs were incubated with A549 cells, mitotic arrest was observed, leading to dramatic cellular morphological changes and cell death (FIGS. 4C and 4F).

Figure 5:
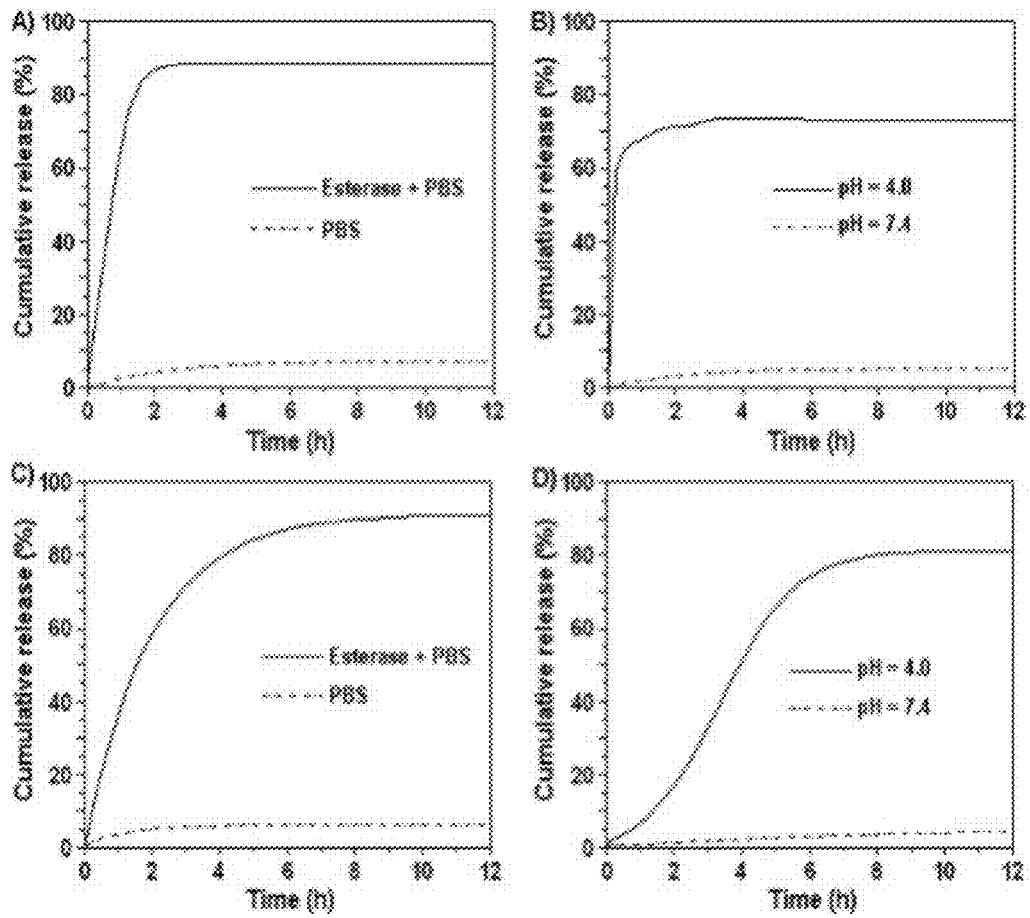
FIG. 5 shows drug and dye release profiles of functional IONPs (5) in PBS (pH=7.4) at 37° C.; release of Taxol® (A & B) and DiI (C & D) was observed in the presence of an esterase enzyme (A & C) and at pH 4.0 (B & D)

The therapeutic application of our nanoparticles depends on the rate of release of the encapsulated drug from the PAA coating. To evaluate 5's drug release profile, enzymatic (esterase) and low-pH degradation experiments were performed. Results indicated a fast release of the drug (Taxol®) from the nanoparticle (5) upon esterase incubation, reaching a plateau within 2 hours (FIG. 5A). An even faster release of the drug was observed at pH 4.0, reaching a plateau within 30 minutes (FIG. 5B). No significant release of the drug was observed from nanoparticles incubated in PBS, pH 7.4. These results are significant as they demonstrate the stability of the nanoparticles during storage (PBS), and their cargo release only after cellular uptake via either esterase-mediated degradation or in acidified lysosomes. Therefore, only after its folate-receptor-mediated uptake, the nanoparticle 5 becomes cytotoxic upon intracellular release of its cargo therapeutic agent. Interestingly, a much slower release of the dye was observed, both upon esterase incubation and at pH 4.0

(FIGS. 5C and 5D). However, no release of the dye was observed at normal physiological pH (7.4). The observed differential release of the drug vs. the dye from IONP 5 may be attributed to the drug's (Taxol®) size and hydrophobic nature.

Taken together, these results make our folate-decorated-IONP (5) an important drug carrier, as it can rapidly release Taxol® and therefore induce cell death only upon targeted cell internalization. Furthermore, the acidic microenvironment of most tumors could enhance the release of Taxol® and dye from the nanoparticle into the tumor to facilitate the monitoring of tumor regression by MR and optical imaging. Also, by modifying the targeting moiety of the theranostic IONP's surface, other carcinomas may be targeted, while obtaining important spatiotemporal information for clinical decision making.

For in vivo imaging applications, nanoparticles with excitation and emission in the near infrared region (650-900 nm) are needed for deep tissue fluorescence imaging.[17] Towards this end, we encapsulated a near infrared dialkylcarbocyanine dye (DiR, excitation/emission:751/780 nm) into the carboxylated (2-DiR) and folate-conjugated (4-DiR) IONPs, following the same synthetic protocol described for the synthesis of IONPs 2 and 4. UV/Vis studies corroborated the presence of the near infrared DiR dye within the nanoparticle's PAA coating (FIG. 11b). To demonstrate the targeting capability of our functional near-infrared and folate-derivatized IONP (4-DiR) to folate receptor expressing cells and eventually assess their intracellular activity, we incubated A549 lung carcinoma cells with the (4-DiR) nanoparticle and imaged the cells using fluorescence imaging techniques.

Figure 16:
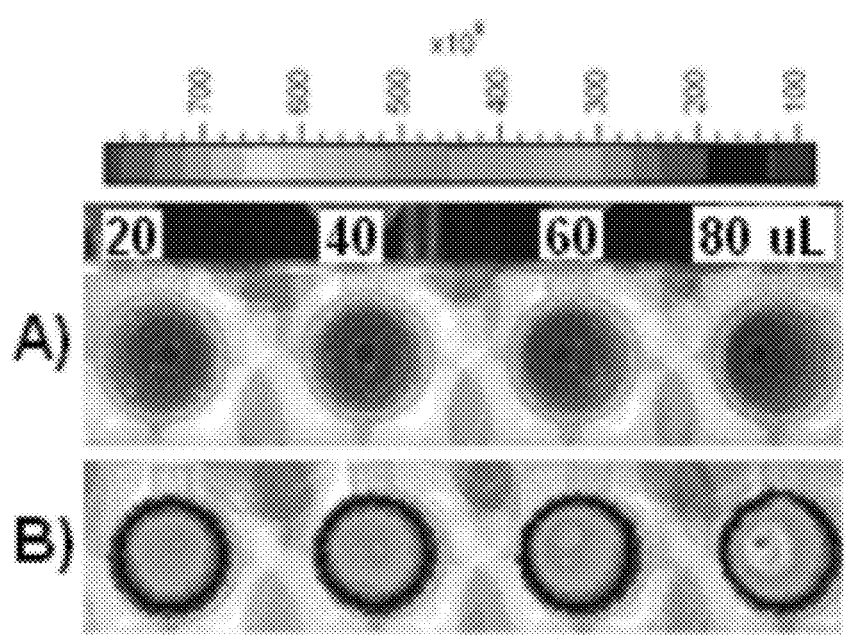
FIG. 16 shows NIR fluorescence imaging of lung carcinoma cells (A549) incubated with (A) carboxylated IONPs (2-DiR) or (B) folate conjugated IONPs (4-DiR); images were taken using an ICG filter.
Figure 17:
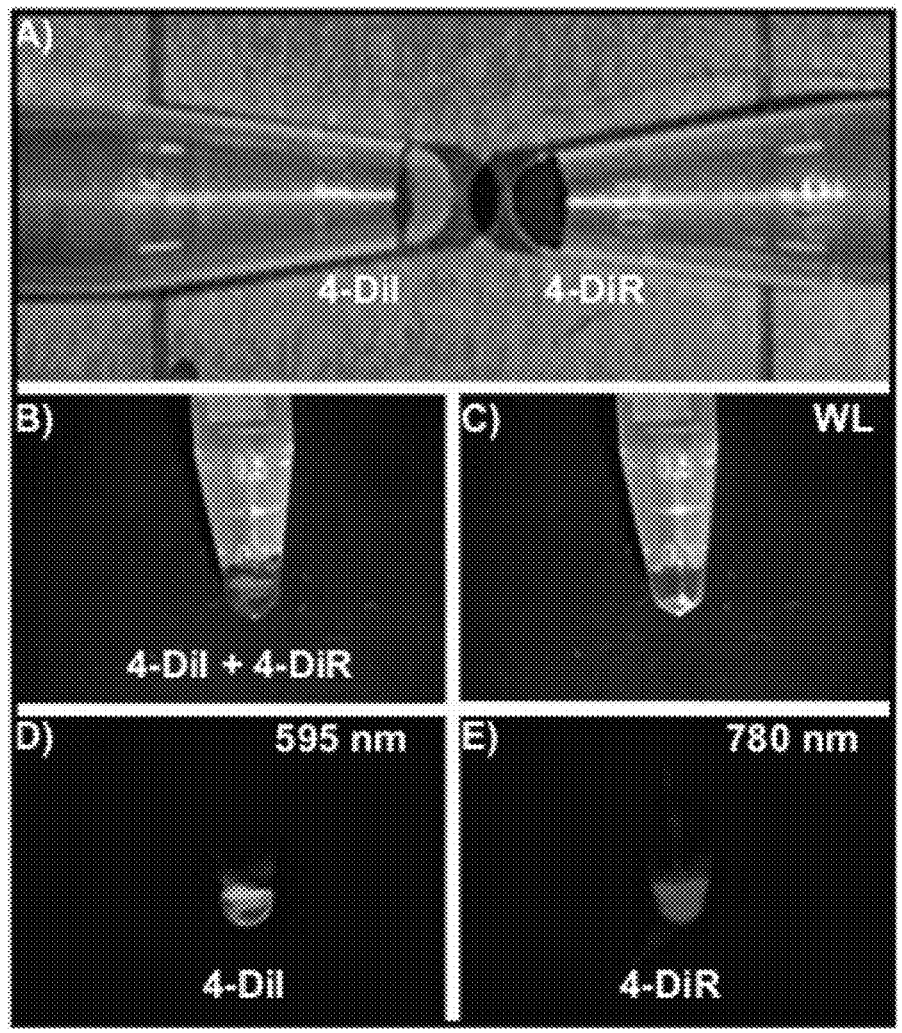
FIG. 17 is a dual image of DiI and DiR wherein (A) is a composite fluorescence optical image of 4-DiI and 4-DiR, taken in separate tubes, showing the imaging capability of the both IONPs; fluorescence images were taken by scanning the entire wavelength from 480 to 920 nm and performing spectral unmixing; (B) Dual image of DiI and DiR using the MAESTRO optical imager; it shows the combined image as an overlay of both images in the lower row (D and E); WL indicates the White Light image; DiI was obtained at 595 nm and DiR at 780 nm.

In these studies, A549 cells (10,000 cells) were treated with either DiR-carrying carboxylated (2-DiR) or DiR-carrying folate-conjugated (4-DiR) IONPs (1.1 mg/mL) for 3 h. Next, the cells were washed with PBS and detached with trypsin. After centrifugation, the resulting cell pellets were simultaneously imaged using an indocyanine green (ICG) filter. No cell-associated near infrared fluorescence was observed in cells treated with the carboxylated (2-DiR) nanoparticles (FIG. 16 panel A). In contrast, a dose-dependent cell-associated DiR fluorescence was observed in cells treated with the folate-conjugated (4-DiR) nanoparticles (FIG. 16 panel B). Since the cells were extensively washed with PBS before imaging and considering the confocal microscopy results shown in FIG. 4, it is plausible that the cells have internalized the (4-DiR) nanoparticles via folate-receptor-mediated endocytosis, thus endowing these cells with near infrared fluorescent. To further confirm the association of these nanoparticles with folate-expressing A549 carcinoma cells, the cell pellets were re-suspended in PBS and their fluorescence emission and MRI signal (T2 relaxation time) were recorded. An increase in fluorescence emission intensity and decrease in magnetic relaxivity (T2) was observed from the corresponding suspension of the cell pellets (Table 3). No fluorescence emission or T2 changes were observed in H9c2 cardiomyocytes treated with 4-DiR. Therefore, these results indicate that our targeted multimodal nanoparticles can simultaneously allow the near infrared fluorescence and MR imaging of folate-receptor expressing cells.

TABLE 3

Determination of fluorescence emission intensity (a.u.) and magnetic relaxivity (T2) of IONP-(4-DiR)-treated cells (A549) in PBS.

| A549 Cell pellets | Cells only | Cells + 20 µL IONPs | Cells + 40 µL IONPs | Cells + 60 µL IONPs | Cells + 80 µL IONPs |
| --- | --- | --- | --- | --- | --- |
| Fl. Emission (×$10^5$) | 0.0 | 1.7 | 2.0 | 2.4 | 2.7 |
| $T_2$ (ms) | 2000 | 165 | 126 | 101 | 78 |

Figure 18:
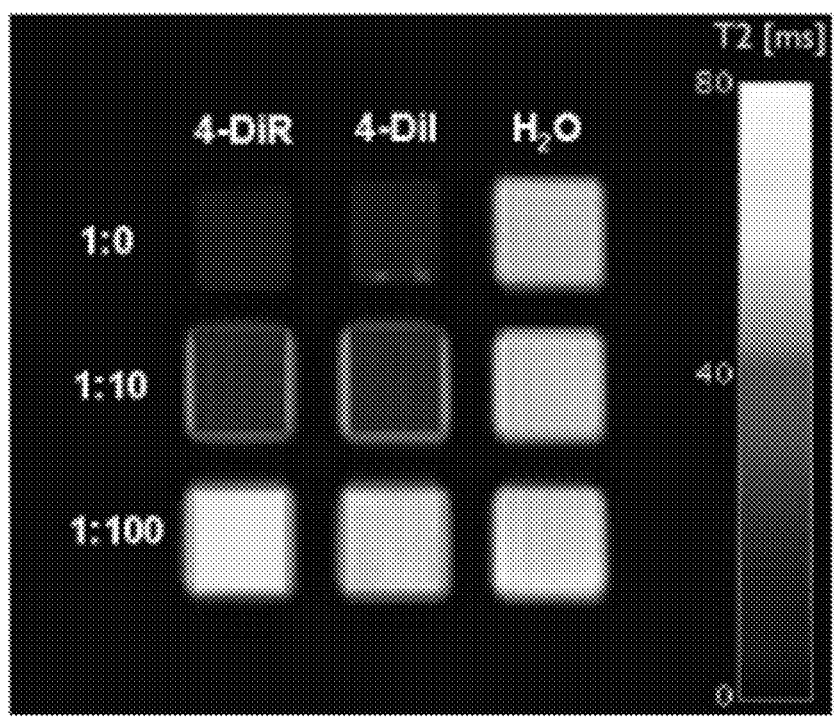
FIG. 18 is an MR image (T2 map) of a PAA-IONP 4 encapsulating either DiI or DiR (4-DiI or 4-DiR); these MR images were obtained by making dilutions from a stock (100 µg/mL) nanoparticle suspension and comparing their MRI signal with that of water; the color bar indicates the T2 relaxation time in ms.

To further assess the utility of the multimodal nanoparticle 4 encapsulating either DiI (4-DiI) or DiR (4-DiR), fluorescence and MRI studies were performed. First, phantoms containing both nanoparticles in PBS were taken using a dedicated optical imaging animal scanner (Maestro, CIR, Woburn, Mass.). Results indicated the potential use of the 4-DiR nanoparticle for near infrared imaging, even in a nanoparticle suspension containing both 4-DiI and 4-DiR IONPs (FIGS. 17A-E). These results are important as they point to the possibility of simultaneously imaging both nanoparticles, which could be utilized in the imaging of two different targets in in vivo experiments (e.g. 2 different cell populations). Furthermore, magnetic resonance imaging (MRI) studies of 4-DiI and 4-DiR nanoparticle dilutions (FIG. 18) using a 4.7T MRI scanner (Bruker, Bellerica Mass.) further demonstrated the ability of these IONPs to behave as sensitive MRI contrast agents.

In conclusion, we introduce a new method to synthesize multimodal and theranostic PAA-IONPs for the potential in vivo target-specific detection and treatment of tumors. Our novel IONPs are biocompatible and biodegradable, as they are synthesized from biodegradable and biocompatible components. These functional IONPs are stable in aqueous buffered solutions, possess good cellular targeting ability, and their simple synthesis process is amenable to scale-up. In addition, this method can easily be used to generate libraries of targeted theranostic nanoparticles with different targeting ligands or encapsulated agents, and even include different metallic cores. Furthermore, the drug-encapsulating IONPs when conjugated with folic acid (using "click" chemistry) provide targeted drug delivery to cancer cells that overexpress the folate receptor, while avoiding normal cells that do not overexpress this receptor. We suggest that this multimodal (magnetic and fluorescent) and multifunctional (imaging and therapeutic) IONPs will open many exciting opportunities for the targeted delivery of therapeutic agents to tumors. In addition, the dual optical and magnetic properties of the synthesized nanoparticles will allow for the dual fluorescence- and MR-based imaging and monitoring of drug efficacy. All these positive attributes make the functional IONPs a promising drug delivery vehicle for further in vivo evaluation.

With the foregoing in mind, those skilled in the art should recognize that when we speak of a "metallic core" we intend a core containing a metal, in any form. Also, the skilled will understand that the hydrophobic pocket(s) formed by the polymeric coat may accept for nesting therein any dye or drug which is compatible with that characteristic, for example, a dye or drug having at least a hydrophobic or lipophilic moiety; it is reasonable to prophetically predict that such dyes and drugs will also work in the invention in addition to those which have been disclosed herein as examples. Dyes which are predicted to work in the invention include, without limitation, cardiogreen, quantum dots, Cy5, Cy5.5, and Alexafluor dyes to mention a few. Metals which are contemplated to work in the invention include the following, although not exclusively, cerium, gold, silver, bismuth, platinum, palladium and their oxides. It should also be understood that in addition to folate groups, amine groups and alcohol groups may also be conjugated on the nanoparticles to provide different targeting specificities. Regarding other drugs which are predicted to work in the invention, these would include anti-HIV drugs, anti-inflammatory drugs, AzT, camptothecin, doxorubicin and others having hydrophobic groups.

Accordingly, in the drawings and specification there have been disclosed typical preferred embodiments of the invention and although specific terms may have been employed, the terms are used in a descriptive sense only and not for purposes of limitation. The invention has been described in considerable detail with specific reference to these illustrated embodiments. It will be apparent, however, that various modifications and changes can be made within the spirit and scope of the invention as described in the foregoing specification and as defined in the appended claims, as set forth below.

LITERATURE CITED

[1] a) J. R. McCarthy, K. A. Kelly, E. Y. Sun, R. Weissleder, Nanomedicine 2007, 2, 153-167; b) A. K. Gupta, M. Gupta, Biomaterials 2005, 26, 3995-4021.
[2] N. Nasongkla, E. Bey, J. Ren, H. Ai, C. Khemtong, J. S. Guthi, S. F. Chin, A. D. Sherry, D. A. Boothman, J. Gao, Nano Lett. 2006, 6, 2427-2430.
[3] a) M. Lewin, N. Carlesso, C. H. Tung, X. W. Tang, D. Cory, D. T. Scadden, R. Weissleder, Nat. Biotechnol. 2000, 18, 410-414; b) L. Josephson, M. F. Kircher, U. Mahmood, Y. Tang, R. Weissleder, Bioconjugate Chem. 2002, 13, 554-560; c) K. C. Weng, C. O, Noble, B. Papahadjopoulos-Sternberg, F. F. Chen, D. C. Drummond, D. B. Kirpotin, D. Wang, Y. K. Horn, B. Hann, J. W. Park, Nano Lett. 2008, 8, 2851-2857.
[4] a) J. H. Choi, F. T. Nguyen, P. W. Barone, D. A. Heller, A. E. Moll, D. Patel, S. A. Boppart, M. S. Strano, Nano Lett. 2007, 7, 861-867; b) W. J. Mulder, R. Koole, R. J. Brandwijk, G. Storm, P. T. Chin, G. J. Strijkers, C. de Mello Donega, K. Nicolay, A. W. Griffioen, Nano Lett. 2006, 6, 1-6.

[5] M. K. Yu, Y. Y. Jeong, J. Park, S. Park, J. W. Kim, J. J. Min, K. Kim, S. Jon, Angew. Chem. Int. Ed. Engl. 2008, 47, 5362-5365.

[6] H. Lee, M. K. Yu, S. Park, S. Moon, J. J. Min, Y. Y. Jeong, H. W. Kang, S. Jon, J. Am. Chem. Soc. 2007, 129, 12739-12745.

[7] H. Lee, E. Lee, K. Kim do, N. K. Jang, Y. Y. Jeong, S. Jon, J. Am. Chem. Soc. 2006, 128, 7383-7389.

[8] S. Peng, C. Wang, J. Xie, S. Sun, J. Am. Chem. Soc. 2006, 128, 10676-10677.

[9] a) J. R. McCarthy, J. M. Perez, C. Bruckner, R. Weissleder, Nano Lett. 2005, 5, 2552-2556; b) B. S. Packard, D. E. Wolf, Biochemistry 1985, 24, 5176-5181.

[10] a) E. Y. Sun, L. Josephson, R. Weissleder, Molecular Imaging 2006, 5, 122-128; b) H. C. Kolb, M. G. Finn, K. B. Sharpless, Angew. Chem. Int. Ed. Engl. 2001, 40, 2004-2021; c) M. A. White, J. A. Johnson, J. T. Koberstein, N. J. Turro, J. Am. Chem. Soc. 2006, 128, 11356-11357.

[11] a) S. Santra, B. Liesenfeld, D. Dutta, D. Chatel, C. D. Batich, W. Tan, B. M. Moudgil, R. A. Mericle, J. Nanosci. Nanotech. 2005, X, 1-6; b) K. Riebeseel, E. Biedermann, R. Lser, N. Breiter, R. Hanselmann, R. Mlhaupt, C. Unger, F. Kratz, Bioconjugate Chem. 2002, 13, 773-785.

[12] M. Shi, J. H. Wosnick, K. Ho, A. Keating, M. S. Shoichet, Angew. Chem. Int. Ed. Engl. 2007, 46, 6126-6131.

[13] a) A. M. Koch, F. Reynolds, M. F. Kircher, H. P. Merkle, R. Weissleder, L. Josephson, Bioconjugate Chem. 2003, 14, 1115-1121; b) T. Shen, R. Weissleder, M. Papisov, A. Bogdanov, Jr., T. J. Brady, Magn. Reson. Med. 1993, 29, 599-604.

[14] N. Parker, M. J. Turk, E. Westrick, J. D. Lewis, P. S. Low, C. P. Leamon, Anal. Biochem. 2005, 338, 284-293.

[15] H. Yuan, J. Miao, Y. Z. Du, J. You, F. Q. Hu, S. Zeng, Int. J. Pharm. 2008, 348, 137-145.

[16] M. E. Nelson, N. A. Loktionova, A. E. Pegg, R. C. Moschel, J. Med. Chem. 2004, 47, 3887-91.

[17] R. Weissleder, V. Ntziachristos, Nat. Med. 2003, 9, 123-128.

That which is claimed:

1. A nanoparticle comprising:
   a metallic core;
   a polymeric coat surrounding said core and forming an outer periphery of said nanoparticle;
   a plurality of hydrophobic pockets formed by the polymeric coat;
   a plurality of carboxylic groups along an outer periphery of the polymeric coat and effective to conjugate with a predetermined targeting ligand which functionalizes the nanoparticle;
   a lipophilic fluorescent dye encapsulated in the plurality of hydrophobic pockets; and
   a drug encapsulated in the plurality of hydrophobic pockets.

2. The nanoparticle of claim 1, wherein the metallic core comprises a metallic oxide.

3. The nanoparticle of claim 1, wherein the metallic core comprises superparamagnetic iron oxide.

4. The nanoparticle of claim 1, wherein said polymeric coat comprises a biodegradable polymer.

5. The nanoparticle of claim 1, wherein said polymeric coat comprises a matrix of polyacrylic acid.

6. The nanoparticle of claim 1, wherein said polymeric coat comprises a biodegradable polymer effective for forming a plurality of hydrophobic pockets.

7. The nanoparticle of claim 1, wherein folate groups are conjugated to the polymeric coat.

8. The nanoparticle of claim 1, wherein folate groups are conjugated to a plurality of carboxylic groups on the polymeric coat.

9. The nanoparticle of claim 1, wherein azide-functionalized folate groups are conjugated to the polymeric coat.

10. The nanoparticle of claim 1, wherein azide-functionalized folate groups are conjugated to the plurality of carboxylic groups on the polymeric coat.

11. The nanoparticle of claim 1, wherein the lipophilic fluorescent dye is selected from the group consisting of dialkylcarbocyanine fluorescent dyes.

12. The nanoparticle of claim 1, wherein the lipophylic fluorescent dye is selected from lipophilic dyes having a near-infrared spectrum.

13. The nanoparticle of claim 1, wherein the lipophilic fluorescent dye is selected from DiI, DiR and 4',6-diamidino-2-phenylindole.

14. The nanoparticle of claim 1, wherein the drug comprises a hydrophobic or lipophilic moiety.

15. The nanoparticle of claim 1, wherein the drug comprises a hydrophobic moiety.

16. The nanoparticle of claim 1, wherein the drug is an anti-cancer therapeutic drug.

17. The nanoparticle of claim 1, wherein the drug is paclitaxel.

18. The nanoparticle of claim 1, wherein the lipophylic fluorescent dye and the drug are co-encapsulated in the plurality of hydrophobic pockets.

19. A method of treatment comprising contacting a cancerous cell with the nanoparticle of claim 1 which has been conjugated with a ligand specific for a receptor expressed by the cancerous cell and wherein the drug is an anti-cancer drug.

20. The method of claim 19, further comprising tracking the nanoparticle by magnetic resonance imaging.

21. The method of claim 19, further comprising tracking the nanoparticle by optical imaging relying on fluorescence.

22. A method of treatment comprising contacting a diseased cell with the nanoparticle of claim 1 which has been conjugated with a ligand specific for a receptor expressed by the diseased cell and wherein the drug is effective for treating the disease afflicting the cell.

23. The method of claim 22, further comprising tracking the nanoparticle by magnetic resonance imaging.

24. The method of claim 22, further comprising tracking the nanoparticle by optical imaging relying on fluorescence.

25. A water based, step-wise method of making polyacrylic acid-coated iron oxide nanoparticles of claim 1, the method comprising:
   preparing an aqueous solution of iron salts by mixing FeCl3 and FeCl2 in dilute hydrochloric acid;
   preparing an alkaline solution by dissolving ammonium hydroxide in deionized water purged with nitrogen gas;
   preparing a coating agent solution by dissolving polyacrylic acid in deionized water;
   reacting by mixing the iron salts solution with the alkaline solution while vigorously stirring the mixture to form a dark suspension of iron oxide nanoparticles;
   adding coating agent solution while stirring;
   separating the iron oxide nanoparticles from the suspension;
   washing the separated nanoparticles in water to minimize free polyacrylic acid and other unreacted reagents;
   purifying the washed nanoparticles through a magnetic column; and
   concentrating the purified nanoparticles.

26. A method of making polyacrylic acid-coated iron oxide nanoparticles of claim 1, the method comprising:

reacting an acidic solution containing Fe+2 and Fe+3 ions with aqueous ammonium hydroxide to form a dark suspension of iron oxide nanoparticles;

mixing aqueous polyacrylic acid with the suspension of iron oxide nanoparticles while stirring for a time sufficient for the nanoparticles to become coated with the polyacrylic acid;

separating coated iron oxide nanoparticles from the mixture; and washing and concentrating the separated nanoparticles.

\* \* \* \* \*

UNITED STATES PATENT AND TRADEMARK OFFICE
CERTIFICATE OF CORRECTION

PATENT NO. : 8,236,284 B1
APPLICATION NO. : 12/416993
DATED : August 7, 2012
INVENTOR(S) : J. Manuel Perez et al.

Page 1 of 1

It is certified that error appears in the above-identified patent and that said Letters Patent is hereby corrected as shown below:

Column 1, Lines 14-17: Cancel the text "Development of the present invention was supported, at least in part, by a grant from the U.S. Government. Accordingly, the Government may have certain rights in the invention, as specified by law." and replace it with the following:
--The invention was made with government support under grant K01CA101781 awarded by the National Institutes of Health. The government has certain rights in the invention.--

Signed and Sealed this
Twelfth Day of March, 2013

Teresa Stanek Rea
*Acting Director of the United States Patent and Trademark Office*